United States Patent [19]

Aufdembrinke et al.

[11] Patent Number: 4,711,891

[45] Date of Patent: Dec. 8, 1987

[54] USE OF TERGURIDE AS A GERIATRIC AGENT

[75] Inventors: Bernd Aufdembrinke; Rainer Dorow; Reinhard Horowski; Irmgard Suchy; Gertrud Schroeder; Helmut Wachtel; Wolfgang Kehr; Günter Stock, all of Berlin, Fed. Rep. of Germany

[73] Assignee: Schering Aktiengesellschaft, Berlin and Bergkamen, Fed. Rep. of Germany

[21] Appl. No.: 872,779

[22] Filed: Jun. 10, 1986

[30] Foreign Application Priority Data

Jun. 24, 1985 [DE] Fed. Rep. of Germany ....... 3522894

[51] Int. Cl.[4] ............................................. A61V 31/47

[52] U.S. Cl. .................................. 514/313; 514/878; 514/879

[58] Field of Search ....................... 514/878, 879, 313

[56] References Cited

U.S. PATENT DOCUMENTS 4,366,157 12/1982 Ono et al. ........................... 514/879
4,552,820 6/1985 Dorow et al. ...................... 428/611

OTHER PUBLICATIONS

Chem. Abst. vol. 97, 1982-1827/6 W.

*Primary Examiner*—Stanley J. Friedman
*Attorney, Agent, or Firm*—Millen & White

[57] ABSTRACT

Terguride and its physiologically compatible salts can be used for the treatment of geriatric deficiencies, e.g., in doses of 0.1–5.0 mg/day.

27 Claims, No Drawings

USE OF TERGURIDE AS A GERIATRIC AGENT

BACKGROUND OF THE INVENTION

The invention relates to a new use for terguride and its physiologically compatible salts.

Terguride [3-(6-methylergolin-8α-yl)-1,1-diethylurea] is a known useful drug, e.g., for its nidation- and lactation-inhibiting as well as antipsychotic effects, e.g., upon oral administration to animal and man. These are believed due to its partial-agonistic action on dopamine receptors. (See, e.g, German Pat. No. 2,238,540 and DOS No. 3,129,714, which are entirely incorporated by reference.)

Furthermore, various other ergot alkaloids, for example, bromocryptine or lisuride, have been used in human medicin for hypertension therapy (Stumpe, K. O., Kolloch, R., Higuchi, M. K., Kruck, F., Vetter, H.: *Hyperprolactinemia nad Antihypertensive Effect of Bromocryptine in Essential Hypertension*, Lancet 2:211, 1977).

It is furthermore known that the neurotransmitter, dopamine, important not only for motor functions but also for psychic, cognitive and endocrine functions, suffers a decrease in effectiveness with increasing age. This occurs not only in test animals but as well in man and is believed due to lowered concentrations in the brain with increasing age (A. Carlsson and Winblad, B., *J. Neural Transmission* 38:271–276, 1976; Severson, J. A. and Finch, C. E., *Brain Research* 192:147–162, 1980). Parkinson's disease has been known for a long time as an extreme form of dopamine deficiency in the motor system. In its therapy, dopamine agonists such as L-dopa and bromocryptine have proven themselves well. However, these compounds have the drawback that they have such a strong effect on all dopamine receptors as to evoke, as side effects, also nausea, vomiting, orthostatic regulatory disturbances, and stupor.

It is likewise known to utilize other ergot alkaloids having a weakly dopaminergic activity—detectable only during long-term treatment, for example as a lowering of prolactin level—such as dihydroergotoxine for therapy in cognitive and vigilance disturbances as well as other disorders of the brain function in the aged (R. J. McDonald, *Pharmacopsychiatry* 12:407–422, 1979). This weakly effective dopamine agonist, however, has the disadvantage that its pronounced α-adrenolytic activity precludes the use of the relatively high doses required for the quick attainment of a stronger therapeutic effect.

It is impossible to provide acutely higher dosages of dihydroergotoxine since in such cases strong orthostatic reactions occur in addition to a lowering of the blood pressure conveyed dopaminergically.

SUMMARY OF THE INVENTION

It is thus an object of the present invention to provide an agent for the improved treatment of geriatric complaints, e.g., those mentioned above, e.g., which is suitable for the treatment of reduced vigilance, worsening state and function of mind, and diminishing psychomotor function, concomitantly caused by restricted dopamine function in the aged, which agent ameliorates or overcomes the above-mentioned deficiencies.

Upon further study of the specification and appended claims, further objects and advantages of this invention will become apparent to those skilled in the art.

These objects have now been achieved surprisingly, e.g., by the finding that terguride affects, at varying initial conditions, dopaminergic neurotransmission in differing ways. Thus, dopamine hypofunction—for example in rats by chronic administration of reserpine, or in Parkinson's disease—can be compensated for by terguride whereas intact dopamine systems are not influenced by comparable doses. Thus, side effects are lower and symptoms due to dopamine receptor over-stimulation as observed with classical dopamine agonists are not to be expected. It is even possible to inhibit, through terguride, systems having dopamine hyperfunction—for example due to amphetamine or lisuride treatment in rats or in Huntington's disease or schizophrenia without disturbing other dopaminergic systems with normal function.

It is not predictable that a compound known as a partial dopamine agonist could be useful in treating even conditions derived from dopamine hypofunctions. This is even more certainly true in predicting the usefulness of such an agent in treating dopamine hyperfunctions. The general unpredictability in this area is clearly shown by the successful use of terguride, the first partial dopamine agonist in clinical tests, in treating conditions derived from dopamine hyperfunction.

It is consequently feasible to utilize terguride to treat cerebral insufficiency in the aged, hypofunctions of dopaminergic systems, etc., to regulate motor function, mood, and vigilance without thereby triggering—as in case of the classical dopamine agonists—difficult to tolerate, subjective side effects.

Thus, one aspect of this invention relates to a method of treating geriatric disorders and/or the disorders mentioned above comprising administering an effective amount of terguride to a patient suffering therefrom. It also relates to geriatric compositions containing terguride. Reduced side effects are a special advantage. The additional ability of terguride to normalize dopamine hyperfunction as well may also become useful if symptoms related to such an overfunction are present (e.g. hypermotility and dyskinesia, psychic disturbances, either from spontaneous origin or caused by concomitant use of dopaminergic drugs, e.g. in Parkinsonism).

DETAILED DISCUSSION

Suitable physiologically compatible salts of terguride include those with inorganic and organic acids. Examples of compounds suitable for salt formation include hydrochloric acid, phosphoric acid, sulfuric acid, methane-sulfonic acid, glucoheptanoic acid, succinic acid, tartaric acid, maleic acid, etc. Many other conventional pharmacologically acceptable salts are useful and well known. A preferred salt is terguride dihydrogen phosphate. Terguride per se is also preferred.

Clinical findings in controlled studies revealed in aged patients having Parkinson's disease that treatment with terguride improved not only motor function but simultaneously also mood and vigilance. In patients having the clinical symptoms of dementia, frequency changes could be confirmed in the electroencephalogram (EEG) running counter to the EEG frequency changes connected with aging.

In aged test volunteers suffering from hypertension, general functional capacity and well-being were not simultaneously impaired by reduction in raised systolic and diastolic blood pressure. A gentle, slowly developing antihypertensive effect without any simultaneously occurring changes in cardiac frequency moreover contributes toward a reduction in vascular complications caused by hypertension.

In all cases, and in contrast to therapy with conventional dopamine agonists, subjective and objective compatibility of terguride was very good. In contradistinction to other therapy, the positive aspects of the treatment manifested themselves as early as in the first few days.

An immediate dopaminergic stimulation by terguride could also be demonstrated by the prolactin-lowering effect of this treatment, an effect that after treatment with dihydroergotoxine occurs only after weeks or months and is then correlated with the clinical therapy success attained with cerebral insufficiency in the aged. No disturbances in orthostatic regulation are observed in the administered doses.

The clinical results are illustrated in the table below.

TABLE

|  | Hydergine (Dihydroergotoxine) | Terguride | Bromocriptine Lisuride |
|---|---|---|---|
| Antihypertensive effect | ++ | ++ | + |
| Prolactin-lowering effect | (+) After weeks | ++ | ++ |
| Nausea, vomiting | − | − | ++ |
| Orthostatism | + | (+) | + |
| Improvement of vigilance | After weeks | After days | Undeterminable due to side effects (activation as well as dysphoria) |
| Improvement of mood | After weeks | After days | |

− not observed at normal dose range
(+) very rarely observed(at higher dosages)
+ effect present(but mostly at higher dosages)
++ effect pronounced at normal dose range The data in the table demonstrate that terguride is more compatible when compared with bromocriptine. In comparison with hydergine, terguride shows higher efficacy, with the effect also manifesting itself faster. Use of terguride causes less orthostatism problems in comparison with both of the two standard compounds.

The utilization of terguride in accordance with this invention, on the one hand, in comparison with the presently available therapies with strong dopamine agonists and their heavy side effects, and on the other hand with the weak dopamine agonist dihydroergotoxine having a strong α-adrenolytic component and effects that are too little and too late (Loew et al., *Aging* 23:227–239, 1983), consequently means a considerable improvement in treating cerebral insufficiency in the aged and other consequences of functional dopamine deficiency.

In medical practice, terguride and its salts can be administered to mammals, including humans, orally and parenterally e.g., subcutaneously, intramuscularly or intravenously. Oral administration is preferred. The daily dosage is 0.1–5.0 mg, preferably 0.25—1.0 mg.

As can be seen, terguride has been discovered to be especially useful in treating geriatric disorders, including an ideopathic decline in mental capacity (e.g., analogously to the conventional ergoloid mesylates, e.g., hydergine and other commercial equivalents), including declines in cognitive and interpersonal skills, mood, self-care, apparent motivation, etc. There is no particular age at which terguride is useful in accordance with this invention. Typically, individuals over 60 will be special candidates. There is no specific minimum or maximum treatment time. Details of a preferred regimen will be in accordance with conventional considerations in view of the usual details of a patient's condition and care, analogously to the administration of known cognition adjuvants and related pharmaceuticals.

The medical terguride specialties can be prepared in a manner known per se by processing terguride with the excipients, diluents, flavoring agents, etc., customary in pharmacy. Suitable for injections are, in particular, aqueous, but also oily solutions as well as suspensions. Terguride can also be administered in galenic forms to achieve stable plasma levels, e.g. by subcutaneous or other infusion using known pump systems in a way as described recently by L. Obeso et al. Such solutions could consist of distilled water, saline or other vehicles preferrably containing 0.01–10 mg/ml. For the production of intramuscular depot formulations, the active agents can be suspended or dissolved in fatty oils according to conventional methods.

The medical agents of this invention are suitable especially in the form of tablets, capsules, dragees, pills, suspension and solutions for oral administration. However, oral sustained-release formulations are also suitable, e.g., as conventionally obtained, for example, by adding hydrogenated fats and processing them with resin-forming agents and lacquers. Drops for oral administration can be prepared as aqueous solutions or suspensions of active agent in oils with the addition of flavoring agents and/or solubilizers.

Oral or parental formulations of terguride can also be mixed with other drugs (e.g. dopamine agonists) in order to enhance efficacy or reduce side effects of these compounds.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating a cognition decline or a decline or disturbance in motor function or vigilance in a geriatric patient comprising administering to the patient an effective amount of terguride or a pharmacologically acceptable salt thereof.

2. A method of treating a decline in mental capacity and function in a geriatric patient comprising administering to the patient an effective amount of terguride or a pharmacologically acceptable salt thereof.

3. A method of claim 1, wherein the dosage is 0.1–5.0 mg/day.

4. A method of claim 2, wherein the dosage is 0.1–5.0 mg/day.

5. A method of claim 1, wherein terguride or a salt thereof is administered in a pharmaceutical composition further comprising a pharmaceutically compatible adjuvant.

6. A method of claim 2, wherein terguride or a salt thereof is administered in a pharmaceutical composition further comprising a pharmaceutically compatible adjuvant.

7. A method of claim 1, wherein the administration is orally.

8. A method of claim 2, wherein the administration is orally.

9. A method of claim 3, wherein the administration is orally.

10. A method of claim 4, wherein the administration is orally.

11. A method of claim 1, wherein the geriatric patient is suffering from a cognition decline.

12. A method of claim 1, wherein the geriatric patient is suffering from a decline or disturbance in motor function or vigilance.

13. A method of claim 1, wherein the administration is parenterally.

14. A method of claim 1 wherein the administration is parenterally.

15. A method of claim 1 wherein the patient is suffering from Parkinson's disease.

16. A method of claim 3 wherein the patient is suffering from Parkinson's disease.

17. A method of claim 1 wherein the patient is suffering from a mood disorder.

18. A method of claim 1 wherein the patient is suffering from dementia.

19. A method of claim 2 wherein the patient is suffering from cerebral insufficiency.

20. A method of treating Parkinsonism in a patient comprising administering to the patient an effective amount of terguride or a pharmaceutically acceptable salt thereof.

21. A method of treating a patient suffering from dopamine hypofunction comprising administering to the patient an effective amount of terguride or a pharmaceutically acceptable salt thereof.

22. A method of claim 21 wherein said terguride or salt thereof simultaneously causes no substantial effect on intact dopamine systems in said patient.

23. A method of claim 21 wherein the patient is suffering from a cognition decline, a decline or disturbance in motor function or vigilance, a decline in mental capacity or function, or a mood disorder.

24. A method of claim 22 wherein the patient is suffering from Parkinson's disease.

25. A method of treating a patient suffering from dopamine hyperfunction, exclusive of psychosis and midation and lactation abnormalities, comprising administering to the patient an effective amount of terguride or a pharmaceutically acceptable salt thereof.

26. A method of claim 25 wherein said terguride or salt thereof simultaneously causes no substantial effect on intact dopamine systems in said patient.

27. A method of claim 26 wherein said dopamine hyperfunction is associated with Huntington's disease, administration of an amphetamine or a dopaminergic drug, hypermotility or dyskinesia.

* * * * *